United States Patent [19]

Schmidt

[11] Patent Number: 4,474,048

[45] Date of Patent: Oct. 2, 1984

[54] CALIBRATING GAS GENERATOR

[75] Inventor: Martin Schmidt, Bad Schwartau, Fed. Rep. of Germany

[73] Assignee: Drägerwerk Aktiengesellschaft, Fed. Rep. of Germany

[21] Appl. No.: 475,478

[22] Filed: Mar. 15, 1983

[30] Foreign Application Priority Data

Apr. 30, 1982 [DE] Fed. Rep. of Germany ....... 3216109

[51] Int. Cl.$^3$ ............................................. G01N 31/00
[52] U.S. Cl. .......................................... 73/1 G; 436/9
[58] Field of Search .............. 73/1 G; 436/9; 261/124

[56] References Cited

U.S. PATENT DOCUMENTS

| | | | |
|---|---|---|---|
| 3,847,551 | 11/1974 | Huston | 73/1 G |
| 3,854,319 | 12/1974 | Burroughs | 73/1 G |
| 3,885,414 | 5/1975 | Reville | 73/1 G |
| 4,003,240 | 1/1977 | Durbin | 73/1 G |
| 4,069,701 | 1/1978 | Baldauf | 73/1 G |
| 4,407,152 | 10/1983 | Guth | 73/1 G |

Primary Examiner—S. Clement Swisher
Attorney, Agent, or Firm—McGlew and Tuttle

[57] ABSTRACT

A calibrating gas generator comprises two series connected solution tanks filled with an aqueous ethanol solution which are connected together so that a pump may direct air so that it successively bubbles through the ethanol solution in each tank and exit through a test nozzle connected to the last tank. Means are provided for maintaining a temperature in the first tank of 37° C. and in the second solution tank of 34° C. In accordance with the method of the invention, the testing reliability of the calibrating gas is extended by directing a gas such as air so that it successively bubbles through ethanol solutions in first and second tanks and by maintaining the solution in the first tank at 37° C. and the solution in the second tank at 34° C.

5 Claims, 2 Drawing Figures

CALIBRATING GAS GENERATOR

BACKGROUND OF THE INVENTION

Field of the Invention

This invention relates, in general, to calibrated gases and their uses and, in particular, to a new and useful calibrating gas generator and to a method of forming a calibrating gas.

Breath-alcohol meters are used increasingly by the police in their patrols. In order to ensure the measuring accuracy, particularly in view of later court proceedings, the breath-alcohol meters are regularly calibrated. To this end is used a calibrator which is of high concentration stability, simple and inexpensive to operate.

A known calibrating gas generator contains two tanks which are filled with an aqueous ethyl alcohol standard. They are thermostated to the same temperature of $34\pm0.2$ deg C. The tanks are series-connected over lines with a pump. The pump conveys ambient air through the filling of the first and subsequently of the second tank. The air absorbs alcohol and water vapor from the liquid, the calibrating gas formed has a defined alcohol concentration which depends on the temperature of the tank. The concentration of the liquid drops, due to the alcohol given off. This effects particularly the first tank. From the second tank is only taken the amount of alcohol which the liquid in the first tank could not absorb, due to the impoverishment of the liquid which had already occurred there. This results in a gradual drop of the liquid concentration in the second tank too, which leads to differences in the concentration of the calibrating gas. Within the framework of the required tolerances, the amount of the calibrating gas that can be produced with a liquid filling must therefore be limited. The frequent replacement of the partly utilized liquid is annoying for the operator, due to the energy expenditure and the waiting periods until it can be operated again, because of the required heating (Operating Instructions 4752.01, Oct. 1981, Draegerwerk AG).

SUMMARY OF THE INVENTION

The invention provides a calibrating gas generator with a high concentration stability over a great number of measurements, which is simple to operate and which remain economical.

According to the invention, the temperature of the aqueous ethanol solution in the first solution tank is 37° C., and in the second solution tank 34° C. Curves I and II show the extended concentration stability. With a maximum deviation of 1% from the initial value (nominal value), the number of tests can be increased from 55 to 110. This means essential advantages for a better utilization of the ethanol solution and the resulting savings in waiting time.

Accordingly, it is an object of the invention to provide a method of generating calibrating gas so that its calibrating life may be extended which comprises directing a carrier gas such as air successively through an ethanol solution in at least two tanks while maintaining a first tank at 37° C. and the second tank at 34° C.

A further object of the invention is to provide a calibrating gas generator which includes two series connected tanks with means for directing air so that it bubbles successively through the liquid in each tank and further including means for maintaining the temperatures of the solutions in each tank at approximately 37° C. in the first tank and 34° C. in the second tank.

A further object of the invention is to provide a calibrating gas generator which is simple in design, rugged in construction and economical to manufacture.

For an understanding of the principles of the invention, reference is made to the following description of typical embodiments thereof as illustrated in the accompanying drawings.

BRIEF DESCRIPTION ON THE DRAWINGS

GENERAL DESCRIPTION OF THE PREFERRED EMBODIMENTS

Figure 1:
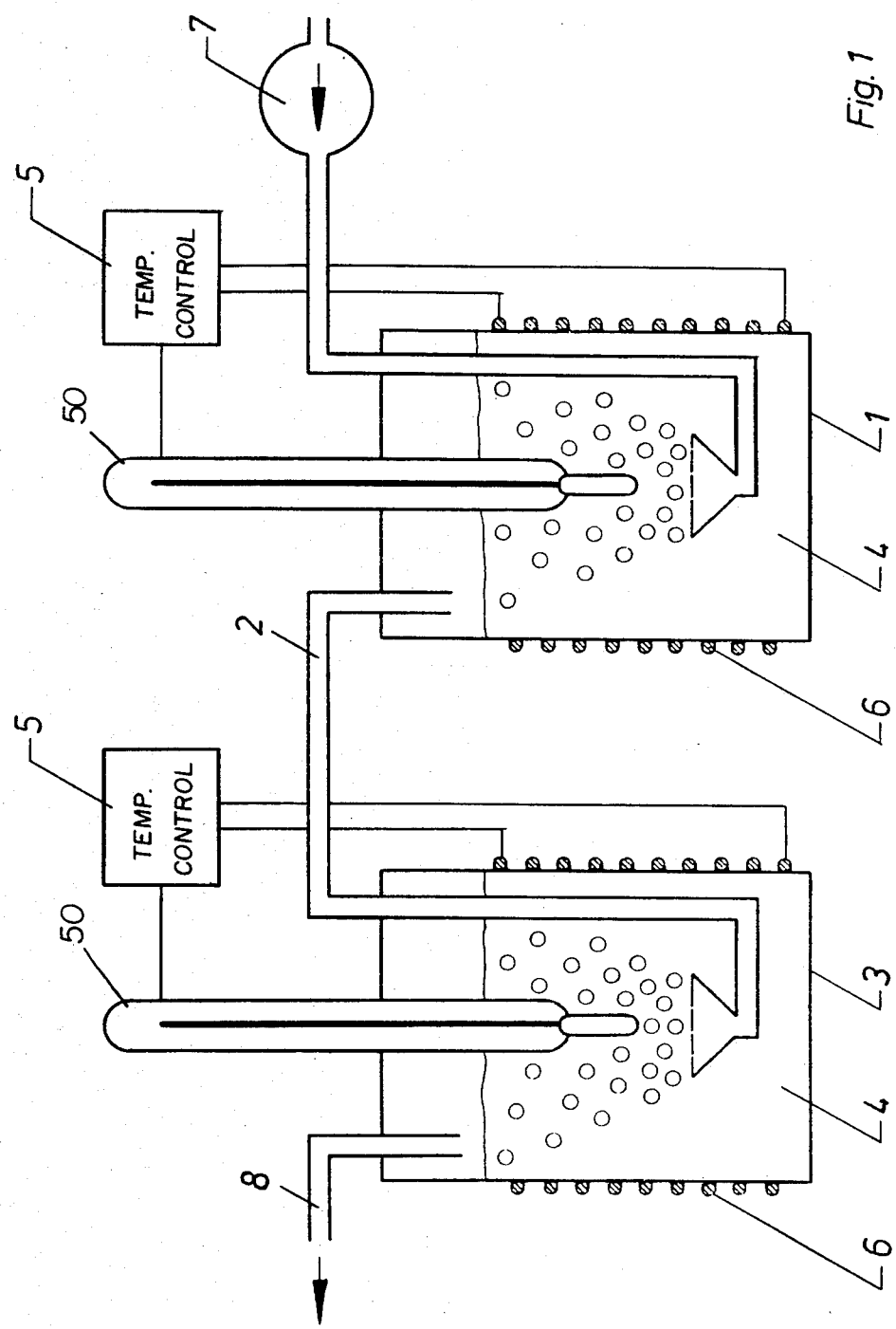
FIG. 1 is a diagrammatical indication of a calibrating gas generator constructed in accordance with the invention.

In accordance with the method of the invention, the carrier gas such as ambient air is pumped by a pump 7 so that it bubbles through an ethanol solution 4 of a first solution type 1 and is then directed through a connecting line 2 so that it bubbles through an ethanol solution 4 of a second tank 3 and is then delivered out to a test nozzle 8. In accordance with the invention, the ethanol solution in the first tank 1 is mainted at 37° C. and in the second tank 3 is maintained at 34° C. The temperature is controlled by a temperature controller 5 which is connected to a heater 6 and is responsive to a temperature sensor 50 disposed in the respective tanks 1 and 3.

The calibrating gas generator contains a first solution tank 1 and a second solution tank 3 connected over a connecting pipe line 2 both filled with an identical aqueous ethanol solution 4. By means of a temperature control 5 and heater 6 for each, the temperature of the aqueous ethanol solution 4 is brought to 37° C. in the first solution tank and is reheated and maintained at 34° in the second solution tank 3.

Ambient air is pumped into the system by means of a pump 7. It flows in fine bubbles through ethanol solution 4 in the first solution tank 1, then through connecting pipe 2 and in the same manner through the second solution tank 3 and leaves the calibrating gas generator through test nozzle 8 to the calibrating breath-control meter.

In operation, the ambient air in the first solution tank 1 is enriched with alcohol and water corresponding to the solution temperature, which ensures the desired vapor pressure. The same procedure takes place in the second solution tank 3.

The higher temperature of 37° C. in the first solution tank 1 leads to greater evaporation than in the second solution tank 3 with a solution temperature at 34° C. This has the effect that more vapor issues at first from the first solution tank 1 than from the second solution tank 3 and that a gradual enrichment of the calibrating substance even takes place in the latter, which compensates, however, later the decrease of the calibrating substance from the first solution tank 1, due to evaporation.

Figure 2:
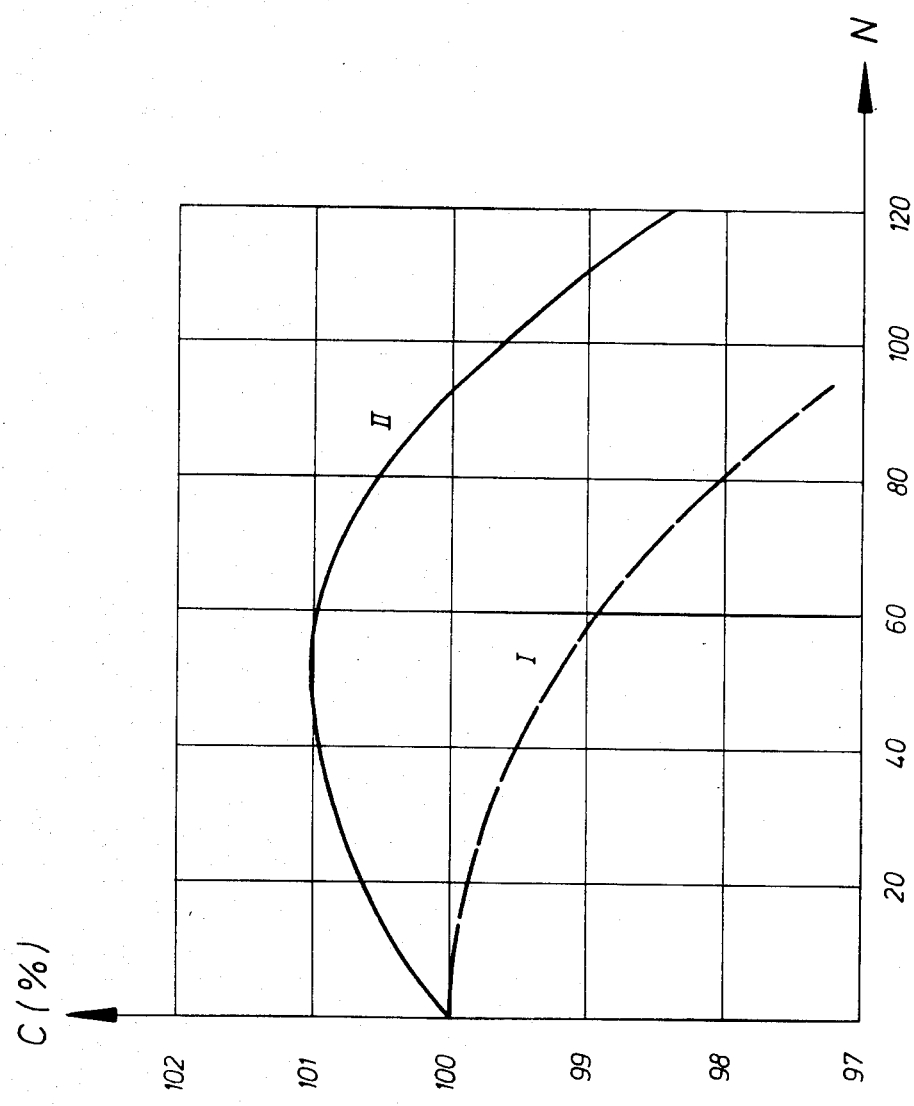
FIG. 2 is a diagram showing the tests made with aqueous ethanol solutions in the variation of the concentration over the test life.

FIG. 2 shows a curve of the mode of operation, N tests were made with an aqueous ethanol solution, and the concentration C of the calibrating gas was measured in percent:

(a) The temperature of ethanol solution 4 in the solution tanks 1 and 3 was the same with 34° C. The broken curve I shows the decrease of the calibrating gas concentration C. A deviation of 1% from the initial value (nominal value) is already obtained after about 55 tests;

(b) The temperature of ethanol solution 4 in the first solution tank is 37° C. and in the second solution tank 34° C. As it can be seen from curve II, the calibrating gas concentration C increases first by 1% to drop then after about 100 tests to 99%.

Breath-alcohol meters are used increasingly by the police in their patrols. In order to ensure the measuring accuracy, the instruments are regularly calibrated. To this end is used a calibrator which should be of high concentration stability.

The calibrating gas generator contains a first solution tank 1 thermostated to a temperature of 37° C. and a following second solution tank 3 connected over a connecting line 2, which is thermostated to 34° C., both filled with an aqueous ethanol solution 4. A pump 5 conveys air, which is conducted successively through the ethanol solution in the first and second solution tank and bubbles toward a test nozzle 6 while it is enriched with alcohol and water corresponding to the vapor pressure.

The different temperatures of 37° and 34° C. in the solution-tanks permit a greater number of possible calibrations before an impoverishment of the ethanol solution takes place.

While specific embodiments of the invention have been shown and described in detail to illustrate the application of the principles of the invention, it will be understood that the invention may be embodied otherwise without departing from such principles.

What is claimed is:

1. A method of generating a calibrating gas so that its testing capability is extended, comprising directing calibrating gas successively through two separate ethanol solutions while maintaining the first solution at 37° C. and the second solution at 34° C.

2. A method according to claim 1, wherein the solutions are maintained in separate tanks and wherein they are maintained at the selected temperatures by a heater.

3. A calibrating gas generator comprising first and second closed tanks each having an aqueous solution of ethanol therein, a conduit connected from the top of said first tank into the solution of said second tank, a nozzle connected from the top of said second tank to the exterior thereof, means for directing air into the solution of said first tank to permit it to bubble through the solution thereof and into the conduit so that it bubbles through the ethanol solution of said second tank for exit through said nozzle, and means for maintaining the aqueous ethanol solution in said first and second tanks at 37° C. and 34° C., respectively.

4. A calibrating gas generator according to claim 3, including a heater associated with each of said tanks, temperature sensing means located in the aqueous ethanol solutions of each tank, the control means connected between said sensing means and said heater for regulating said heater in accordance with the temperatures of the respective aqueous ethanol solutions to maintain them at the respective 37° C. and 34° C. temperatures.

5. A calibrating gas generator comprising two series connected thermostated solution tanks each filled with an aqueous ethanol solution, a pump connected into said tanks for directing air into each tank so that it successively bubbles through the ethanol solution in the respective tanks, a test nozzle connected to the second tank for directing the air which bubbles through the aqueous ethanol solutions out of said tanks, and means for maintaining the temperature in the aqueous ethanol solutions of said first tank and said second tank at 37° C. and 34° C., respectively.

* * * * *